United States Patent [19]
Samain et al.

[11] Patent Number: 6,083,494
[45] Date of Patent: Jul. 4, 2000

[54] COSMETIC COMPOSITION COMPRISING AN AQUEOUS NON-IONIC POLYMER DISPERSION AND PROCESS OF USING

[75] Inventors: Henri Samain, Bievres; Daniel Bauer, Le Raincy, both of France

[73] Assignee: L'Oreal, Paris, France

[21] Appl. No.: 08/693,640

[22] Filed: Aug. 9, 1996

[30] Foreign Application Priority Data

Aug. 11, 1995 [FR] France ................... 95-09772

[51] Int. Cl.[7] ............... A61K 7/06; A61K 7/11
[52] U.S. Cl. ................... 424/70.11; 424/70.15; 424/70.16; 424/70.17
[58] Field of Search ............... 424/40, 401, 43, 424/44, 47, 486, 487, 497, 498, 502, 70.22, 70.12, 70.11, DIG. 1–3, 70.1, 70.16, 70.31, 70.15, 70.17; 514/772.1, 772.4; 524/516

[56] References Cited

U.S. PATENT DOCUMENTS

| | | | |
|---|---|---|---|
| 4,085,264 | 4/1978 | Seib et al. | 526/47 |
| 4,845,204 | 7/1989 | Lang et al. | 536/20 |
| 4,874,811 | 10/1989 | Borchers et al. | 524/516 |
| 5,139,037 | 8/1992 | Grollier et al. | 132/203 |
| 5,160,730 | 11/1992 | Dubief et al. | |
| 5,306,484 | 4/1994 | Potthoff-Karl et al. | |
| 5,441,728 | 8/1995 | Tsaur et al. | 424/70.11 |
| 5,514,302 | 5/1996 | Brown | 252/545 |
| 5,540,910 | 7/1996 | Samain et al. | 424/70.51 |

FOREIGN PATENT DOCUMENTS

| | | |
|---|---|---|
| 0288012 | 10/1988 | European Pat. Off. |
| 0320218 | 6/1989 | European Pat. Off. |
| 0323715 | 7/1989 | European Pat. Off. |
| 0379082 | 7/1990 | European Pat. Off. |
| 0424260 | 4/1991 | European Pat. Off. |
| 0590604 | 4/1994 | European Pat. Off. |
| 2351135 | 12/1977 | France |
| 2697160 | 4/1994 | France |
| 4314305 | 11/1994 | Germany |
| WO-A-9221316 | 12/1992 | WIPO |
| WO-A-9528909 | 11/1995 | WIPO |

OTHER PUBLICATIONS

English language Derwent Abstract of FR–A–2697160, Apr. 29, 1994.

English language Derwent Abstract of DE–A–4314305, 1994.

Chemical Abstracts, vol. 89, No. 14, p. 517, Abstract No. 117546m, Oct. 2, 1978, "Hair–Setting Preparations".

*Primary Examiner*—Paula K. Hutzell
*Assistant Examiner*—Brenda G. Brumback
*Attorney, Agent, or Firm*—Finnegan, Henderson, Farabow, Garrett & Dunner, L.L.P.

[57] ABSTRACT

An aqueous or aqueous/alcoholic cosmetic composition comprising an aqueous dispersion of insoluble particles of a non-ionic film-forming polymer, the polymer particles being at a concentration greater than 15% by weight with respect to the total weight of the composition and the glass transition temperature of the polymer particles of the composition ranging from 15 to 35° C. and a process for the cosmetic treatment of keratinous substances using these compositions.

20 Claims, No Drawings

COSMETIC COMPOSITION COMPRISING AN AQUEOUS NON-IONIC POLYMER DISPERSION AND PROCESS OF USING

The present invention is directed to an aqueous or aqueous/alcoholic cosmetic composition comprising an aqueous dispersion of insoluble particles of a non-ionic film-forming polymer, the polymer particles being present at a concentration greater than 15% by weight of the composition and the glass transition temperature of the polymer particles of the composition ranging from 15° to 35° C. The present invention also relates to a cosmetic treatment process using these compositions.

Hair compositions to be sprayed or vaporized onto hair are essentially composed of a solution, most often aqueous/alcoholic, and a polymer, optionally as a mixture with various other cosmetic adjuvants. This solution is packaged either in a pump-action spray or in an appropriate aerosol container which is pressurized using a propellant gas.

For a number of years, particular interest has been directed towards producing essentially aqueous cosmetic hair compositions. In fact, the use of alcohol, such as ethanol or isopropanol, alone or as a mixture with a small proportion of water, can exhibit a number of disadvantages, in particular an increase in flammability when the composition is in the form of an aerosol lacquer.

More generally still, attempts are being made to reduce the use of compounds known as VOCs (Volatile Organic Compounds), which are volatile at atmospheric pressure, and which are present in cosmetic compositions. The VOCs are mainly propellants and certain solvents, such as ethanol.

In order to decrease the amount of VOCs present in cosmetic compositions, attempts have been made to replace solvents, such as ethanol, by water. However, while the majority of water-soluble film-forming polymers can, in solution in water, result in the production of hair fixing compositions, the latter exhibit major disadvantages. Thus, the essentially aqueous compositions of these polymers do not make it possible to obtain high degrees of fixing. It has certainly been proposed to use these water-soluble polymers at high concentrations but the increase in concentration causes such an increase in the viscosity of the compositions that it is only with great difficulty that satisfactory spraying can be obtained. Even if correct spraying is obtained, these aqueous compositions exhibit a particularly long drying time with respect to alcoholic compositions.

It has also been proposed to use aqueous dispersions of insoluble particles of anionic polymers instead of the soluble polymers used in aqueous, aqueous/alcoholic, or alcoholic compositions. However, to date, the results obtained are still unsatisfactory. In fact, the degree of fixing is still insufficient, the drying time is long, and the cosmetic properties are not quite good enough.

A search is therefore still under way for aqueous compositions capable of resulting in properties analogous to those of compositions with a high alcohol content, namely good diffusion during application, a good fixing power, resistance to moisture, good removal on shampooing and on brushing and a good rate of drying.

The Inventors have discovered that a cosmetic composition comprising, in a cosmetically acceptable aqueous or aqueous/alcoholic medium, an aqueous dispersion of insoluble non-ionic polymer particles, the polymer particles being present at a concentration greater than 15% by weight with respect to the total weight of the composition and the glass transition temperature of the polymer particles of the composition ranging from 15 to 35° C., makes it possible to overcome the disadvantages described above.

In particular, the compositions according to the invention make it possible to obtain a good shape-retention power which is better than that obtained with an aqueous dispersion of an anionic polymer.

The subject of the present invention is therefore a cosmetic composition comprising, in a cosmetically acceptable aqueous or aqueous/alcoholic medium, an aqueous dispersion of insoluble non-ionic polymer particles, the polymer particles being present at a concentration greater than 15% by weight with respect to the total weight of the composition, and the glass transition temperature of the polymer particles of the composition ranging from 15° to 35° C.

The compositions according to the invention exhibit, in addition to the above-mentioned advantages, good resistance to moisture, good removal on shampooing and on brushing and a good rate of drying.

Other characteristics, aspects and advantages of the invention will become more apparent on reading the detailed description which follows and the concrete, but in no way limiting, examples intended to illustrate the invention.

The aqueous dispersions of insoluble non-ionic polymer particles which can be used according to the invention are preferably obtained by suspension or emulsion polymerization or copolymerization of monomers according to processes which are well known in the state of the art (such dispersions are also known as "latexes").

The aqueous dispersions can result, in particular, from the polymerization or copolymerization of monomers such as, for example, styrene, butadiene, ethylene, propylene, vinyltoluene, vinyl propionate, vinyl alcohol, acrylonitrile, chloroprene, vinyl acetate, urethanes, isoprene, isobutene, the esters or amides of acrylic, methacrylic, maleic, crotonic or itaconic acids, vinyl ether, vinylpyrrolidone and vinylimidazole.

The aqueous dispersions which can be used according to the invention can arise from the condensation of ionic or non-ionic monomers giving non-ionic polymers, such as, for example, polyesters, polyamides, polyurethanes and polyethers.

The aqueous dispersions which are particularly preferred in the context of the invention are aqueous dispersions of styrene/butyl acrylate copolymers, such as, for example, the product sold under the trade name Uramul SC 70 by the company D.S.M. Resins.

The concentration by weight of the polymer particles in the compositions according to the invention preferably ranges from greater than 15% up to a concentration no greater than that at which the polymer particles can be maintained in an aqueous dispersion. More preferably, the concentration by weight of the polymer particles in the compositions of the invention ranges from greater than 15% to 50% by weight with respect to the total weight of the composition, and still more preferably ranges from greater than 15% to 35% by weight.

The pH of the compositions according to the invention preferably ranges from 2 to 9, and more preferably ranges from 3 to 8. The pH can be adjusted to the desired value by means of basifying or acidifying agents commonly used in cosmetics for this type of application.

When the composition according to the invention is pressurized in the form of an aerosol, the aerosol comprises the composition described above, known as juice, and at least one propellant agent which can be chosen from volatile hydrocarbons, such as n-butane, propane, isobutane or pentane, chlorinated and/or fluorinated hydrocarbons and mixtures thereof. It is also possible to use, as a propellant agent, carbon dioxide gas, nitrous oxide, dimethyl ether, nitrogen, compressed air and mixtures thereof.

In such a system, the concentration of propellant(s) preferably ranges from 1 to 50% by weight with respect to the total weight of the pressurized composition, and more preferably ranges from 15 to 35% by weight.

According to a preferred embodiment of the invention, the concentration of polymer particles is at least 10% by weight with respect to the weight of the pressurized composition (juice+propellant), and can more preferably range up to a concentration no greater than that at which the polymer particles can be maintained in an aqueous dispersion, and still more preferably ranges from 10 to 35% by weight.

The propellant agents are preferably present in foams in proportions of less than 25% by weight with respect to the total weight of the composition and more preferably in proportions ranging from 1% to 10%.

The cosmetically acceptable aqueous or aqueous/alcoholic medium, which is used as a vehicle for the compositions according to the invention, is preferably composed of water or an aqueous/alcoholic solution composed of water and at least one monoalcohol, such as, for example, lower alcohols such as ethanol, isopropanol or butanol, at least one polyalcohol, or at least one glycol ether, which can be used alone or as a mixture. More preferably, the vehicle is essentially composed of water.

The compositions according to the invention (in the pressurized or unpressurized state) can additionally contain surface-active agents, preserving agents, sequestrants, softeners, fragrances, dyes, viscosity-modifying agents, foam-modifying agents, antifoaming agents, pearlescence agents, moisturizing agents, antidandruff agents, antiseborrhoeic agents, sunscreening agents, proteins, vitamins, plasticizers, hydroxy acids or electrolytes.

The compositions according to the invention can also contain conditioning agents. The conditioning agents may be chosen from natural or synthetic oils and waxes, fatty alcohols, esters of polyhydric alcohols, glycerides, silicone gums and resins or mixtures of these various compounds.

Of course, the person skilled in the art will be careful to choose the optional compound or compounds to be added to the composition according to the invention so that the advantageous properties intrinsically attached to the composition in accordance with the invention are not, or not substantially, detrimentally affected by the envisaged addition.

The compositions used according to the invention are, for example, rinsed or non-rinsed hair compositions. They are more particularly hair setting lotions, lotions for blow drying, fixing compositions (lacquers), styling compositions, foams or gels. The lotions can be packaged in various forms, in particular in atomizers or pump-action sprays or in aerosol containers, in order to ensure application of the composition in the vaporized form.

A further subject of the invention is a process for the cosmetic treatment of keratinous substances, such as hair, which comprises applying to the keratinous substances a cosmetic composition as defined above and then optionally rinsing with water, after an optional setting time.

In the following example, "AM" means active material.

EXAMPLE

A composition A, according to the invention, was prepared and was compared with a composition B, not in accordance with the invention. These two compositions differ from one another in the nature of the polymer used.

Both compositions were pressurized as aerosols. A panel of 5 experienced testers evaluated the shape-retention power of the hair after drying at room temperature. The shape-retention power is the ability of the composition to maintain the hair in the desired shape.

The grading ranged from 0 (bad) to 5 (excellent).

The results are collated in the table below:

| In g AM | A (Invention) | B (Comparative) |
|---|---|---|
| Uramul SC 70[1] | 18 | — |
| Amerhold DR 25[2] | — | 18 |
| Water, q.s for | 100 | 100 |
| Shape-retention power of the pressurized composition | 4.5 | 3 |

(1): Uramul SC 70 from D.S.M. Resins: Non-ionic styrene/butyl acrylate copolymer (Tg ~30° C.) as an aqueous dispersion containing 50% of active material (2) Amerhold DR 25 from Amerchol: anionic ethyl acrylate/methyl methacrylate/methacrylic acid/acrylic acid copolymer having a glass transition temperature of approximately 30° C. as an aqueous dispersion containing 25% by weight of AM.

The pressurization scheme was as follows:

| dimethyl ether (propellant) | 35 g |
| composition above (juice) | 65 g |

The composition A according to the invention exhibited a shape-retention power which was markedly greater than that of the composition B which was not in accordance with the invention.

What is claimed is:

1. A cosmetic composition, which comprises, in a cosmetically acceptable aqueous or aqueous/alcoholic medium, an aqueous dispersion of insoluble non-ionic polymer particles, wherein said polymer particles are present at a concentration greater than 15% by weight with respect to the total weight of the composition, wherein the glass transition temperature of said polymer particles of said composition ranges from 15 to 35° C., and further wherein the composition has a pH ranging from 2 to 9, and does not include water soluble film-forming polymeric particles.

2. A composition according to claim 1, wherein said aqueous dispersion results from the polymerization or copolymerization of monomers selected from styrene, butadiene, ethylene, propylene, vinyltoluene, vinyl propionate, vinyl alcohol, acrylonitrile, chloroprene, vinyl acetate, urethanes, isoprene, isobutene, vinyl ether, vinylpyrrolidone, vinylimidazole and esters or amides of acrylic acid, methacrylic acid, maleic acid, crotonic acid and itaconic acid.

3. A composition according to claim 2, wherein said aqueous dispersion results from the copolymerization of styrene and butyl acrylate.

4. A composition according to claim 1, wherein the non-ionic polymer of said aqueous dispersion is selected from polyesters, polyamides, polyurethanes and polyethers.

5. A composition according to claim 1, wherein the concentration by weight of said polymer particles ranges from greater than 15% to 50% with respect to the total weight of the composition.

6. A composition according to claim 4, wherein the concentration by weight of said polymer particles ranges from greater than 15% to 35% with respect to the total weight of the composition.

7. A composition according to claim 1, wherein said composition is a hair setting lotion, a lotion for blow drying hair, a lacquer, a foam or a gel.

8. A process for cosmetically treating keratinous substances, which comprises the step of applying to said keratinous substances a cosmetically effective amount of a cosmetic composition as claimed in claim 1.

9. A process according to claim 8, which comprises the further step of rinsing the treated keratinous substances with water.

10. A process according to claim 9, which comprises the further step of allowing said treated keratinous substances to set prior to said step of rinsing with water.

11. A composition according to claim 1, wherein said composition has a pH ranging from 3 to 8.

12. A pressurized aerosol composition, which comprises at least one propellant agent, and, in a cosmetically acceptable aqueous or aqueous/alcoholic medium, an aqueous dispersion of insoluble non-ionic polymer particles, wherein said polymer particles are present at a concentration of at least 10% by weight with respect to the total weight of the pressurized aerosol composition, wherein the glass transition temperature of the polymer particles of said pressurized aerosol composition ranges from 15 to 35° C., and further wherein the composition has a pH ranging from 2 to 9, and does not include water soluble film-forming polymeric particles.

13. A pressurized aerosol composition according to claim 12, wherein said at least one propellant agent is selected from volatile hydrocarbons, chlorinated hydrocarbons, fluorinated hydrocarbons, carbon dioxide gas, nitrous oxide, dimethyl ether, nitrogen, and compressed air.

14. A pressurized aerosol composition according to claim 13, wherein said volatile hydrocarbons are selected from n-butane, propane, isobutane and pentane.

15. A pressurized aerosol composition according to claim 12, wherein the concentration by weight of said polymer particles ranges from 10 to 35% with respect to the total weight of the pressurized aerosol composition.

16. A pressurized aerosol composition according to claim 12, wherein said at least one propellant agent is present in a concentration ranging from 1 to 50% by weight with respect to the total weight of the pressurized aerosol composition.

17. A pressurized aerosol composition according to claim 16, wherein said at least one propellant agent is present in a concentration ranging from 15 to 35% by weight with respect to the total weight of the pressurized aerosol composition.

18. A process for cosmetically treating keratinous substances, which comprises applying to said keratinous substances a cosmetically acceptable amount of a pressurized aerosol composition as claimed in claim 12.

19. A pressurized aerosol composition according to claim 12, wherein said at least one propellant agent is present in the form of foam in a proportion of less than 25% by weight with respect to the total weight of the pressurized aerosol composition.

20. A pressurized aerosol composition according to claim 19, wherein said at least one propellant agent is present in the form of foam in a proportion ranging from 1 to 10% by weight with respect to the total weight of the pressurized aerosol composition.

* * * * *

UNITED STATES PATENT AND TRADEMARK OFFICE
CERTIFICATE OF CORRECTION

PATENT NO. : 6,083,494
DATED : July 4, 2000
INVENTOR(S) : Samain et al.

Page 1 of 1

It is certified that error appears in the above-identified patent and that said Letters Patent is hereby corrected as shown below:

<u>Column 5, claim 6,</u>
Line 1, delete "claim 4" and insert therefor -- claim 5 --.

Signed and Sealed this

Eighteenth Day of September, 2001

Attest:

*Nicholas P. Godici*

NICHOLAS P. GODICI
*Attesting Officer*   *Acting Director of the United States Patent and Trademark Office*